United States Patent [19]

Aubert et al.

[11] Patent Number: 5,728,392

[45] Date of Patent: Mar. 17, 1998

[54] COSMETIC AND/OR DERMATOLOGICAL COMPOSITION FOR THE TREATMENT OF AGING, CONTAINING CERAMIDES, AND THE USE THEREOF

[75] Inventors: Lucien Aubert, Cap d'Ail; Francoise Gagnebien-Cabanne, Chatillon, both of France

[73] Assignee: L'Oreal, Paris, France

[21] Appl. No.: 659,667

[22] Filed: Jun. 5, 1996

Related U.S. Application Data

[63] Continuation of Ser. No. 366,760, Dec. 30, 1994, Pat. No. 5,589,178.

[30] Foreign Application Priority Data

Jan. 10, 1994 [FR] France ................... 94 00173

[51] Int. Cl.⁶ ............... A61K 6/00; A61K 31/615; A61K 31/19; A61K 31/16; A61K 31/07

[52] U.S. Cl. ............... 424/401; 514/162; 514/557; 514/625; 514/627; 514/725

[58] Field of Search ............... 424/401; 514/162, 514/627, 625, 557, 725

[56] References Cited

U.S. PATENT DOCUMENTS

| | | | |
|---|---|---|---|
| 5,368,857 | 11/1994 | Corcoran et al. | 424/401 |
| 5,411,734 | 5/1995 | Vargas et al. | 424/401 |
| 5,443,840 | 8/1995 | Morancais et al. | 424/450 |

*Primary Examiner*—Raymond J. Henley, III
*Attorney, Agent, or Firm*—Oblon, Spivak, McClelland, Maier & Neustadt, P.C.

[57] ABSTRACT

Cosmetic or dermatological compositions containing at least one anti-aging active agent having an irritant effect, a cosmetically or dermatologically acceptable medium, and in addition, as an agent mollifying the irritant effect, a ceramide of the following formula (I):

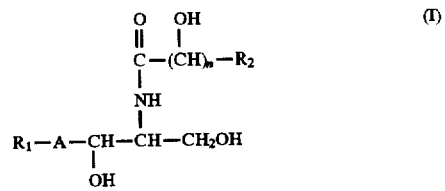

wherein A is

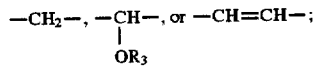

$R_1$ is a saturated or unsaturated, linear or branched $C_{10}$ to $C_{26}$ alkyl group;

$R_2$ is a saturated or unsaturated, linear or branched $C_{12}$ to $C_{32}$ alkyl group;

$R_3$ is H or —CO—CHOH—$R_2$; and n is 0 or 1, are effective for combating the aging of skin and at the same time exhibit a reduced tendency to cause smarting, itching, or a sensation of tightness when applied to the skin.

8 Claims, 2 Drawing Sheets

COSMETIC AND/OR DERMATOLOGICAL COMPOSITION FOR THE TREATMENT OF AGING, CONTAINING CERAMIDES, AND THE USE THEREOF

This is a Continuation of application Ser. No. 08/366,760 filed on Dec. 30, 1994, now U.S. Pat. No. 5,589,178.

BACKGROUND OF THE INVENTION

1. Field of the Invention

The present invention relates to a gentle method for combating aging of the skin of the face and/or the human body, including the scalp and to a process for the cosmetic treatment of wrinkles and fine lines. The present invention also relates to compositions useful in such methods.

2. Discussion of the Background

The effort to look younger and less wrinkled, using cosmetic compositions containing active agents capable of combating aging, is on the increase. The anti-aging active agents commonly used are α-hydroxy acids (lactic, glycolic, citric), β-hydroxy acids (salicyclic, 5-n-octanoylsalicylic acid) and retinoids (all-trans- or 13-cis-retinoic acid, retinol).

Unfortunately, these anti-aging active agents suffer from the major drawback of causing smarting, itching and sensations of tightness after their application, which can lead to considerable discomfort. Hence, the use of these compounds for users having sensitive skin is often ruled out.

Thus, there remains a need for a method for combating aging which does not possess these drawbacks. There also remains a need for compositions which are effective for combating aging but do not cause smarting, itching or a sensation of tightness when applied to the skin.

SUMMARY OF THE INVENTION

Accordingly, it is one object of the present invention to provide a novel method for combating the aging of the skin of the face and body, including the scalp.

It is another object of the present invention to provide a method for combating the aging of the skin which is gentle.

It is another object of the present invention to provide a method for combating the aging of the skin which has a reduced tendency to cause smarting, itching, or a sensation of tightness.

It is another object of the present invention to provide a method for the treatment of wrinkles and fine lines of the skin, which is gentle and has a reduced tendency to cause smarting, itching, or a sensation of tightness.

It is another object of the present invention to provide novel compositions which are useful in such methods.

It is another object of the present invention to provide novel cosmetic and/or dermatological compositions which are effective for combating aging of the skin and treating wrinkles and fine lines of the skin and which are gentle and have a reduced tendency to cause smarting, itching, or a sensation of tightness.

These and other objects, which will become apparent during the following detailed description have been achieved by the inventors' discovery that cosmetic or dermatological compositions containing at least one anti-aging active agent having an irritant effect, a cosmetically or dermatologically acceptable medium, and a ceramide of the following formula (I) as an agent mollifying the irritant effect:

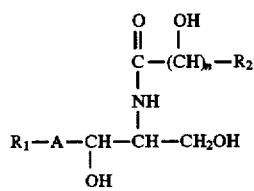

wherein A is

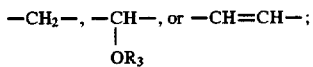

$R_1$ is a saturated or unsaturated, linear or branched $C_{10}$ to $C_{26}$ alkyl group;

$R_2$ is a saturated or unsaturated, linear or branched $C_{12}$ to $C_{32}$ alkyl group;

$R_3$ is H or —CO—CHOH—$R_2$; and n is 0 or 1, are effective for combating the aging of skin and the treatment of wrinkles and fine lines and at the same time are gentle and exhibit a reduced tendency to cause smarting, itching, and a sensation of tightness.

Thus, the presence of the ceramides of formula (I) affords a gentle anti-aging composition which may be applied topically to the skin of the face and/or the human body.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
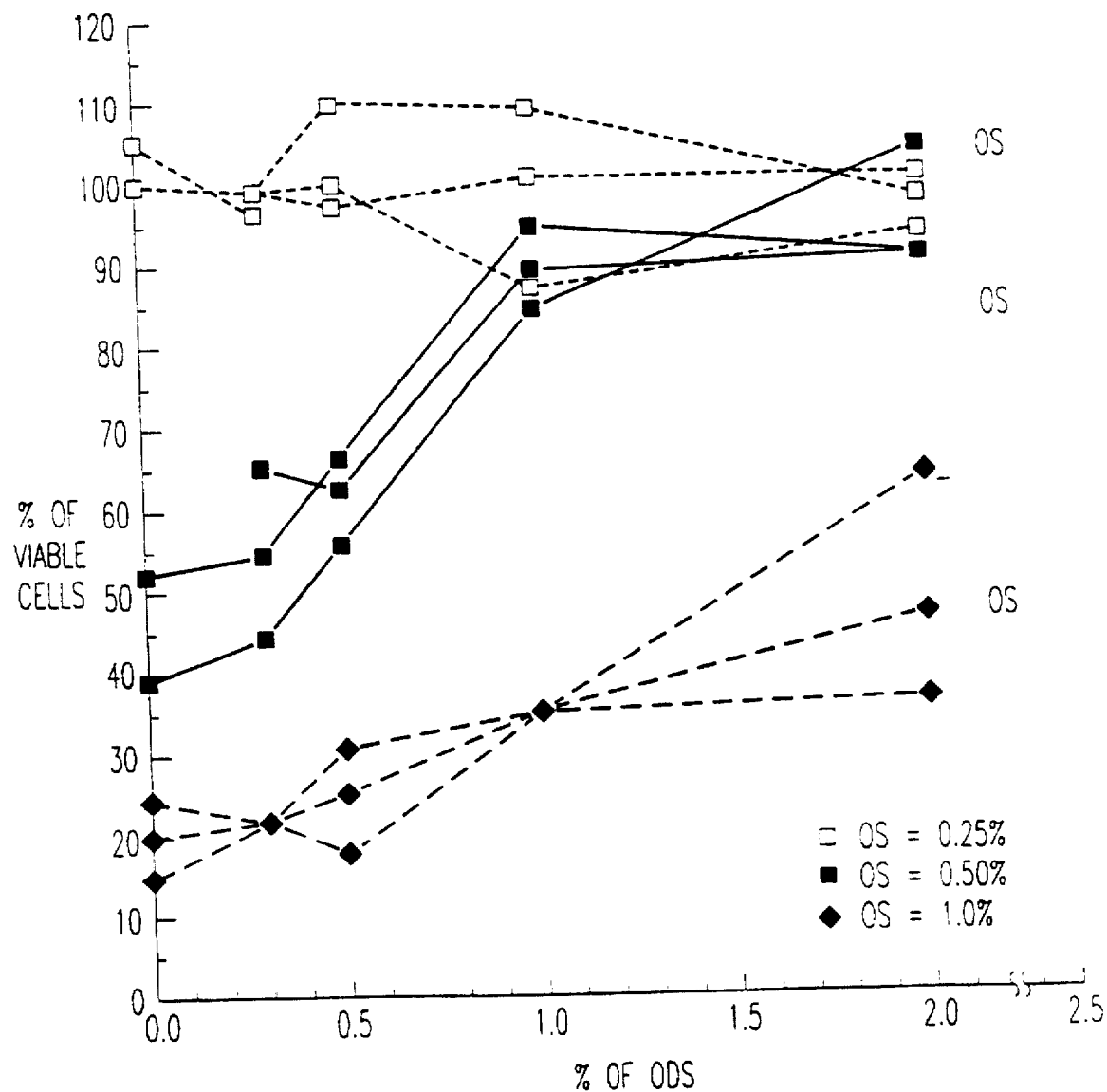
FIG. 1 shows the modulation of cytotoxicity of 5-n-octanoylsalicylic acid (OS) on reconstructed skin by N-oleoyldihydrosphingosine (ODS) (♦, 1.0% by weight OS; ◘, 0.50% by weight OS; and ■, 0.25% by weight OS)

Ceramides occupy a major position, most especially in the upper layers of the epidermis, that is to say in the stratum corneum. There are several types of ceramides, depending on their localization and their function within the epidermis. The term ceramide, taken in its strict sense, comprises only lipids consisting of a sphingosine linked to a fatty acid or fatty acid derivative via its amine function.

The ceramides in the stratum corneum are made up of 6 chromatographically distinct fractions, having a different polarity according to the degree of unsaturation (which can be zero) or hydroxylation of their chains, their length and their number.

According to the present invention, it is possible to use one or more ceramides of formula (I), optionally combined with other types of ceramides, as mollifying agents. Furthermore, the compositions of the present invention can contain one or more anti-aging active agents of identical or different kinds.

The ceramides used in particular in the compositions of the present invention can be of natural origin or synthetic, and may be of type II (for example N-oleoyldihydrosphingosine), of type III (for example N-stearoylphytosphingosine), of type IV (for example N-(α-hydroxybehenoyl)dihydrosphingosine) or of type V (for example N-(α-hydroxypalmitoyl)dihydrosphingosine). It is also possible to use the mixtures of ceramides present in the skin, described by Downing (*The Journal of Investigative Dermatology*, vol. 84, pp. 410–412 (1985)).

It is also possible to use as mollifying agent a preparation containing, in addition to these mixtures of ceramides, cholesterol, free fatty acids such as oleic acid, triglycerides such as triolein and squalene, in order to arrive at a mixture mimicing the epidermal lipids. This preparation may be used at a concentration ranging from 0.01 to 10% by weight, and preferably from 0.05 to 5% by weight, based on the total weight of the composition of the present invention.

From these simple ceramides, it is possible, in addition, to use complex ceramides which can have properties similar to those of the simple ceramides. In particular, sphingolipids such as oligoglycoceramides (gangliosides), monoglycoceramides (cerebrosides), acylmonoglycoceramides, and hydroxyacylmonoglycoceramides may be used. Sphingophospholipids such as sphingomyeline may also be used.

These simple or complex ceramides can be of vegetable origin, such as, for example, the wheat glycoceramides sold by the company ARD or a mixture of glycolipids (containing glycoceramides, phospholipids and triglycerides) sold under the trade name CERAMIDE VEGETAL by the company INOCOSM.

The amount of mollifying agent used in the present invention depends on the amount of anti-aging active agent used. The mollifying agent/anti-aging active agent weight ratio can, for example, be chosen to be from 0.0001:1 to 100,000:1, preferably from 0.01:1 to 1000:1. Moreover, the amount of anti-aging active agent is in practice from 0.0001 to 20% by weight, preferably from 0.01 to 10% by weight, based upon the total weight of the present composition.

The present composition may contain any anti-aging active agent possessing an irritant effect. Examples of active agents to which the invention applies include α-hydroxy acids or β-hydroxy acids, which can be linear, branched or cyclic, saturated or unsaturated. The hydrogen atoms of the carbon chain can, in addition, be substituted with halogens or halogenated alkyl, acyl, acyloxy, alkoxycarbonyl or alkoxy radicals having from 2 to 18 carbon atoms.

As α-hydroxy acids which can be used in the present invention, glycolic, lactic, malic, tartaric, citric and mandelic acids may be mentioned. As β-hydroxy acids, salicylic acid as well as its acylated derivatives such as those described in FR-A-2581542 and EP-A-378986, such as 5-n-octanoylsalicylic acid and 5-n-dodecanoylsalicylic acid, and 2-hydroxyalkanoic acids, and their derivatives such as 2-hydroxy-3-methylbenzoic acid and 2-hydroxy-3-methoxybenzoic acid, may be mentioned.

It is also possible to use as active agents α- or β-keto acids, retinoids, anthralin, anthranoids (for example those described in EP-A-319,028), peroxides such as benzoyl peroxide, minoxidil, capsaicin, lithium and/or zinc salts, antimetabolites such as 5-fluorouracil and vitamins such as vitamin C.

The retinoids to which the invention applies are, in particular, retinol, all-trans- or 13-cis-retinoic acids, retinaldehyde or the compounds mentioned in FR-A-2,676,052, EP-A-210,929, EP-A-292,348, EP-A-199,636, FR-A-2,570,377, FR-A-2,590,566, FR-A-2,601,359, EP-A-325,540, EP-A-232,199, EP-A-552,282, EP-A-284,288, EP-A-170,105 and FR-A-2,422,677.

The compositions of the present invention can, in addition, contain a vegetable, mineral (petrolatum), silicone (cyclomethicone), fluorinated (perfluoro polyether) or synthetic (purcellin oil) oil, an aqueous phase, hydrophilic adjuvants such as gelling agents (clay, xanthan gum), hydrating agents, cicatrizing agents such as glycerol and allatoin as well as their derivatives and compositions containing them, antioxidants (vitamin E), preservatives, opacifying agents, lipophilic adjuvants such as essential oils, colorants, and perfumes, as well as pigments (titanium or zinc oxides) and fillers. The present composition may also contain hydrophilic or lipophilic screening agents, for screening out visible and/or ultraviolet rays, as well as dermatological active agents. These adjuvants may be present in a total amount of from 0.1 to 10% by weight, preferably from 1 to 5% by weight, based on the total weight of the composition.

The compositions according to the present invention can take the form of an oily solution, an aqueous gel, a serum, a lotion, a water-in-oil (W/O) or oil-in-water (O/W) emulsion and/or a dispersion of lipid vesicles (ionic or nonionic).

For an emulsion, a (W/O) or (O/W) emulsifying system is used, as appropriate. When a dispersion of lipid vesicles is used, these latter can constitute the emulsifying system. The emulsifying system is typically present in an amount of from 0.1 to 10% by weight, preferably 1 to 5% by weight, based on the total weight of the composition.

As an (O/W) emulsifier which can be used in the present invention, there may be mentioned PEG-50 stearate and PEG-40 stearate, sold, respectively, under the trade names MYRJ 53 and MYRJ 52 by the company ICI, and sorbitran tristearate sold under the trade name SPAN 65 by the company ICI.

As a (W/O) emulsifier which can be used in the present invention, there may be mentioned the polyglyceryl-4 isostearate/cetyldimethicone copolyol/hexyl laurate mixture sold under the trade name ABIL WE 09 by the company GOLDSCHMIDT, and isostearyl diglyceryl succinate sold under the trade name IMWITOR 780 K by the company H ULS.

In another embodiment, the present invention also provides a method for the treatment of acne, wrinkles and/or fine lines on the skin, as well as a process for combating aging of the skin, by applying to the skin an effective amount of the present composition defined above.

Other features of the invention will become apparent in the course of the following descriptions of exemplary embodiments which are given for illustration of the invention and are not intended to be limiting thereof.

EXAMPLES

In all the following examples, the amounts are given in % by weight, based on the total weight of the composition. The term "qs 100" means that a sufficient quantity of that ingredient is present so that the sum of the amounts for all ingredients totals 100% by weight.

Example 1

| Fatty phase: | |
|---|---|
| Cetyl alcohol | 7 |
| Glyceryl stearate | 2.5 |
| PEG-50 stearate | 2.5 |

| -continued | |
|---|---|
| Groundnut oil (mollifying agent) | 6.2 |
| Isopropyl myristate | 3 |
| N-Oleoyldihydrosphingosine (mollifying agent) | 0.5 |
| Salicylic acid (active agent) | 0.5 |
| Aqueous phase: | |
| Alcohol | 6 |
| Water | qs 100 |

Example 2: O/W emulsion

| Phase A: | |
|---|---|
| 5-n-Octanoylsalicylic acid | 1.0 |
| N-Oleoyldihydrosphingosine | 0.1 |
| Sweat almond oil | 14.1 |
| Shea butter | 7.0 |
| PPG-3 myristyl ether (EMCOL 249-3K) (co-emulsifier and solvent) | 5.0 |
| Preservative (propylparaben) | 0.1 |
| Polysorbate 60 (TWEEN 60) | 2.5 |
| Sorbitan stearate (SPAN 60) | 2.5 |
| Phase B: | |
| Cyclomethicone | 4.0 |
| Xanthan gum | 0.2 |
| Carboxyvinyl polymer | 0.5 |
| Phase C: | |
| Triethanolamine (neutralizing agent) | 0.5 |
| Water | 2.0 |
| Phase D: | |
| Preservative (methylparaben) | 0.2 |
| Glycerol | 5.0 |
| Water | qs 100 |

Procedure:

The constituents of phase A are melted at 85° C., phase A is then cooled to 70° C. and phases B, and then C and D are introduced into it with stirring. The mixture is cooled to room temperature. A hydrating day cream is obtained, which acts against the natural aging of the skin.

TESTS ON RECONSTRUCTED SKIN (MATTEK System)

The cytotoxicity (3-(4,5-dimethyl-2-thiazolyl)-2,5-diphenyltetrazolium bromide test) of emulsions according to Example 2, containing different percentages of 5-n-octanoylsalicylic acid, 0.25%, 0.5% and 1%, respectively, in the presence of increasing concentrations of N-Oleoylidihydrosphingosine, 0%, 0.25%, 0.50%, 1% and 2%, respectively, on a reconstructed epidermis obtained by inoculating human keratinocytes onto a collagen-coated Millipore filter was studied.

100 mg of emulsion are incubated for 3 hours on the reconstructed epidermis (with each measurement carried out in duplicate), and the cell viability is then measured immediately after rinsing off the emulsion with phosphate-buffered saline (PBS).

Figure 2:
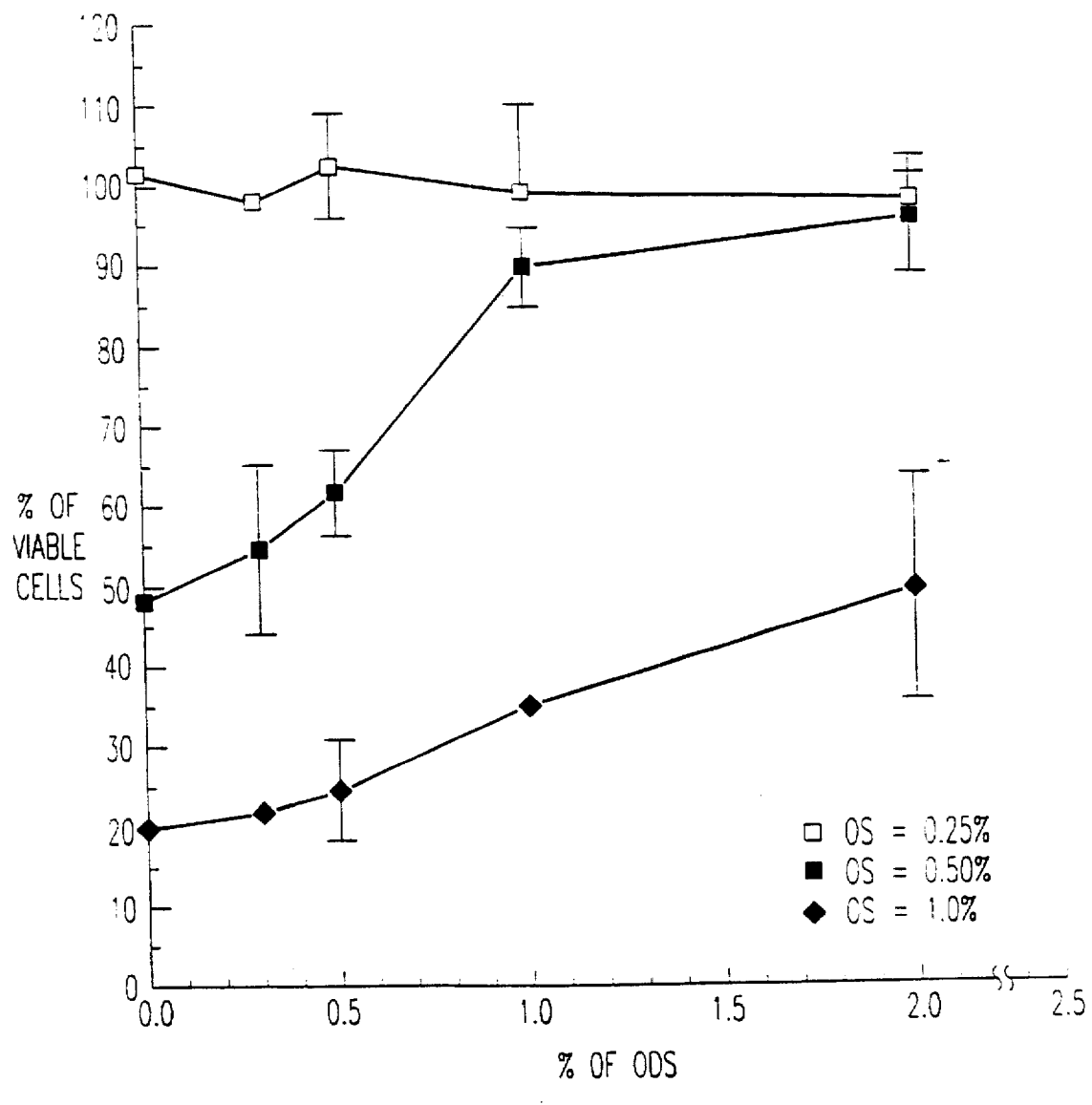
FIG. 2 shows the modulation of cytotoxicity of 5-n-octanoylsalicylic acid (OS) on reconstructed skin by N-oleoyldihydrosphingosine (ODS) (♦, 1.0% by weight OS; ◘, 0.50% by weight OS; and ■, 0.25% by weight OS).

The experiment was carried out two times on three different batches. FIG. 1 presents the individual results for each batch and FIG. 2 shows the mean for the three batches. The results obtained on the three batches are in agreement:

after 3 hours of incubation, the emulsions containing 0.25% of 5-n-octanoylsalicylic acid do not display cytotoxicity;

in the presence of 0.5% of 5-n-octanoylsalicylic acid, a dose-dependent effect of N-oleoyldihydrosphingosine on cell viability becomes apparent. This effect permits considerable protection of cell viability, which in the absence of N-oleoyldihydrosphingosine is 50%, and in the presence of 2% of N-oleoyldihydrosphingosine reaches its maximum level (100% cell viability);

the concentration of 1% of 5-n-octanoylsalicylic acid is very cytotoxic after 3 hours of incubation; only 20% of viable cells remain. This cytotoxicity is nevertheless decreased by the incorporation of N-oleoyldihydrosphingosine in the composition. In effect, the mean cytotoxicity obtained with 2% of N-oleoylidihydrosphingosine is then very close to 50%.

This application is based on French Patent Application 94-00173, filed on Jan. 10, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for mollifying the irritant effect of an anti-aging agent, comprising incorporating in a cosmetic or dermatological composition, comprising at least one anti-aging active agent having an irritant effect and a cosmetically or dermatologically acceptable medium consisting of at least one of an oily or fatty solvent and an aqueous solvent, said oily or fatty solvent selected from the group consisting of oily or fatty alcohols, ethers, hydrocarbons and mixtures thereof, a mollifying agent which is a ceramide of formula (I):

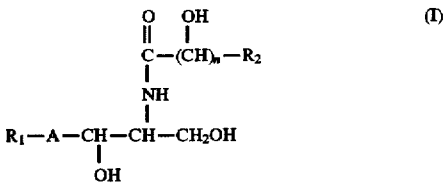

wherein A is

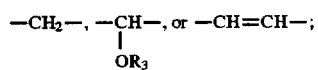

$R_1$ is a saturated or unsaturated, linear or branched $C_{10}$ to $C_{26}$ alkyl group;

$R_2$ is a saturated or unsaturated, linear or branched $C_{12}$ to $C_{32}$ alkyl group;

$R_3$ is H or —CO—CHOH—$R_2$; and n is 0 or 1.

2. The method of claim 1, wherein said mollifying agent is selected from the group consisting of N-oleoyldihydrosphingosine, N-stearoylphytosphingosine, N-(α-hydroxybehenoyl)dihydrosphingosine, and N-(α-hydroxypalmitoyl)dihydrosphingosine.

3. The method of claim 1, wherein said anti-aging active agent is selected from the group consisting of α-hydroxy acids, β-hydroxy acids, α-keto acids, β-keto acids, retinoids, anthraline, anthranoids, peroxides, monoxidil, capsaicin, lithium and zinc salts, antimetabolites and vitamins.

4. The method of claim 1, wherein said anti-aging active agent is selected from the group consisting of α-hydroxy acids, 5-n-octanoylsalicylic acid, and salicylic acid.

5. The method of claim 1, wherein said mollifying agent is present in said composition in a mollifying agent/anti-aging active agent weight ratio ranging from 0.0001:1 to 100,000:1.

6. The method of claim 1, wherein said composition is in the form of a lotion, an aqueous gel, a serum, an emulsion, or a dispersion of lipid vesicles.

7. The method of claim 1, wherein said composition further comprises a lipophilic or hydrophilic active agent different from said anti-aging active agent.

8. A method for mollifying the irritant effect of an anti-aging agent, comprising incorporating in a cosmetic or dermatological composition, comprising at least one anti-aging active agent having an irritant effect and a cosmetically or dermatologically acceptable medium, a mollifying agent which is a ceramide of formula (I):

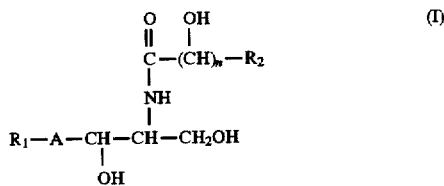

wherein A is

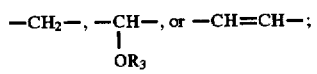

$R_1$ is a saturated or unsaturated, linear or branched $C_{10}$ to $C_{26}$ alkyl group;

$R_2$ is a saturated or unsaturated, linear or branched $C_{12}$ to $C_{32}$ alkyl group;

$R_3$ is H or —CO—CHOH—$R_2$; and n is 0 or 1, the mollifying agent being the only component present to remove the irritant effect.

* * * * *